United States Patent [19]

Dietrich et al.

[11] Patent Number: 4,675,436

[45] Date of Patent: Jun. 23, 1987

[54] PREPARATION OF ALKYL ESTERS OF $\alpha,\beta$-MONOOLEFINICALLY UNSATURATED MONOCARBOXYLIC ACIDS

[75] Inventors: Gerhard Dietrich; Gerhard Nestler, both of Ludwigshafen; Peter Ruckh, Mannheim; Reinhard Herzog, Ludwigshafen, all of Fed. Rep. of Germany

[73] Assignee: BASF Aktiengesellschaft, Fed. Rep. of Germany

[21] Appl. No.: 857,052

[22] Filed: Apr. 29, 1986

[30] Foreign Application Priority Data

May 23, 1985 [DE] Fed. Rep. of Germany ....... 3518482

[51] Int. Cl.$^4$ ..................... C07C 67/08; C07C 69/533
[52] U.S. Cl. .................................................... 560/205
[58] Field of Search ............................... 560/205, 218

[56] References Cited

U.S. PATENT DOCUMENTS 2,822,348  2/1958  Haslam ................................ 560/217
2,917,538  12/1959  Carlyle ............................... 560/205
4,280,009  7/1981  Erpenbach et al. ................ 560/205

FOREIGN PATENT DOCUMENTS 573175  11/1945  United Kingdom ................ 560/218
960005  6/1964  United Kingdom .

*Primary Examiner*—Bernard Helfin
*Assistant Examiner*—L. Hendriksen
*Attorney, Agent, or Firm*—Oblon, Fisher, Spivak, McClelland & Maier

[57] ABSTRACT

Alkyl esters of $\alpha,\beta$-monoolefinically unsaturated monocarboxylic acids are prepared by esterifying the monocarboxylic acid with an alcohol of 6 to 20 carbon atoms in the presence of from 0.1 to 5% by weight, based on the reaction mixture, of a strong acid and in the presence of a polymerization inhibitor and an oxygen-containing gas, at from 80° to 150° C., by a process in which the molar ratio of the monocarboxylic acid to the alcohol is from 1:0.8 to 1:1.2, and the water of reaction is separated off from the reaction mixture while passing an inert gas containing from 1 to 20% by volume of oxygen through the reaction mixture.

1 Claim, No Drawings

PREPARATION OF ALKYL ESTERS OF α,β-MONOOLEFINICALLY UNSATURATED MONOCARBOXYLIC ACIDS

The present invention relates to a process for the preparation of alkyl esters of α,β-monoolefinically unsaturated carboxylic acids, in particular of acrylic and methacrylic acid, by esterification of the acid with an alcohol of 6 to 20 carbon atoms in the presence of a strong acid.

For the large-scale industrial production of alkyl acrylates and methacrylates, essentially two methods are used, i.e.

1. the alkali-catalyzed transesterification of esters of lower alcohols and acrylic or methacrylic acid, e.g. methyl or ethyl acrylate, with an alcohol of higher molecular weight, e.g. 2-ethylhexanol, as disclosed in, for example, U.S. Pat. No. 2,822,348, British Pat. No. 960,005 or German Published Application DAS No. 1,067,805, or
2. the esterification of acrylic or methacrylic acid with an alcohol, which is catalyzed by a strong acid, as described in, for example, U.S. Pat. No. 2,917,538 or German Pat. No. 2,548,561.

In the transesterification processes, the lower alkyl carboxylate, e.g. the acrylate or methacrylate, is used in excess with respect to the alcohol of higher molecular weight, is distilled off from the reaction mixture in order to separate off the resulting lower alcohol, and is recycled to the reaction mixture after the lower alcohol has been separated off. In this process, however, it is frequently difficult to separate off the lower alcohol and the alkaline catalyst used, and the process has therefore not become important in practice.

The reaction of an α,β-monoolefinically unsaturated carboxylic acid, such as acrylic or methacrylic acid, with an alcohol, for example with formation of the alkyl acrylate or methacrylate, is an equilibrium reaction. The conversion is thus determined by the equilibrium constant. Hence, to achieve a high conversion, a large excess of monocarboxylic acid or alcohol is required, or the water formed during the reaction (water of reaction) must be separated off from the reaction mixture by azeotropic distillation, with the addition of an auxiliary liquid, or must be bound to an added drying agent. However, the addition of further starting materials, e.g. an entraining agent, constitutes a considerable disadvantage since the said agent has to be purified by an expensive distillation procedure in order to be able to recycle it to the process.

In the process described in German Pat. No. 2,548,561, the direct esterification can also be carried out without an additional entraining agent, by reacting the acrylic or methacrylic acid with an excess of 2-ethylhexanol in the presence of from 0.2 to 5% by weight of sulfuric acid and a polymerization inhibitor, if appropriate in combination with air, at from 85° to 140° C. under reduced pressure (from 50 to 200 mm Hg), the 2-ethylhexanol used in excess acting as the entraining agent for the azeotropic distillation of the water. Particular disadvantages of this version of the process are that the procedure has to be carried out under reduced pressure, which makes it technically very complicated, and an excess of 2-ethylhexanol must be used, resulting in increased formation of by-products, which are expensive to separate off. The principal by-products formed are ethers and olefins from the 2-ethylhexanol employed, and adducts from the acrylic or methacrylic acid or their esters with 2-ethylhexanol. A technically complicated distillation is required in order to separate off the ethers and olefins, this being necessary in order to prevent these by-products from accumulating as a result of recycling of the excess 2-ethylhexanol, which is a necessary step. Furthermore, the adducts obtained as a distillation residue have to be incinerated or dumped (cf. the comparative experiment described in German Pat. No. 2,548,561).

We have found that alkyl esters of α,β-monoolefinically unsaturated monocarboxylic acids can advantageously be prepared by esterifying the monocarboxylic acid with an alcohol of 6 to 20 carbon atoms in the presence of from 0.1 to 5% by weight, based on the reaction mixture, of a strong acid and in the presence of a polymerization inhibitor and an oxygen-containing gas, at from 80° to 150° C., if the molar ratio of the α,β-monoolefinically unsaturated monocarboxylic acid to the alcohol is from 1:0.8 to 1.2 and the water of reaction is separated off from the reaction mixture while passing an inert gas containing from 1 to 20% by volume of oxygen through the reaction mixture. The novel process is generally carried out under atmospheric pressure, i.e. without increasing or reducing the pressure. In general the water of reaction and a small amount of the alcohol are distilled off via the top of a distillation column mounted on the reaction vessel, the alcohol separated off being recycled to the reaction vessel via the column. The process is preferably carried out continuously, a cascade of 2 or more reaction vessels advantageously being used, and the α,β-monoolefinically unsaturated monocarboxylic acid and the alcohol in a molar ratio of from 1:0.8 to 1:0.98 being fed to the first reaction vessel, and the remaining alcohol being introduced into the further reaction vessels. The reaction time or residence time is in general from 1 to 20 hours, and the product can be worked up in a conventional manner, in particular by distillation.

Preferred, -monoolefinically unsaturated monocarboxylic acids for the novel process are acrylic and methacrylic acid. Other suitable acids are crotonic acid and α-methylcrotonic acid. α,β-monoolefinically, unsaturated monocarboxylic acids of this type are of 3 to 5 carbon atoms.

Particularly suitable alcohols for the novel process are alkanols and alkanediols, such as n-hexanediol, n-octanol, iso-octanol, 2-ethylhexanol, n-decanol, dodecyl alcohol, hexadecanol or octadecanol, the alcohols being substituted or unsubstituted; suitable substituted alkanols are benzyl alcohol, phenyl ethyl alcohol, diethylene glycol monoethyl ether and tripropylene glycol. The strong acid used in the novel process is generally sulfuric acid or para-toluenesulfonic acid, although benzenesulfonic acid, naphthsolulfonic acids and methanesulfonic acid are also suitable.

Examples of suitable polymerization inhibitors which are generally used in amounts of from 100 to 1000 ppm, based on the α,β-monoolefinically unsaturated carboxylic acid, are phenothiazine, methylene blue, parabenzophenone, hydroquinone and hydroquinone monomethyl ether. A particularly suitable oxygen-containing inert gas has proven to be air which may furthermore be diluted with nitrogen down to an oxygen content of 1% by volume. The oxygen-containing inert gas should in general be passed through the reaction mixture during the entire duration of the esterification reaction. In general, from 100 to 600 parts by volume of the inert gas

3 per part of reaction mixture per hour are sufficient for this purpose.

The novel process has the advantage that it can be carried out under atmospheric pressure, without a significant excess of alcohol and in the absence of an additional entraining agent, and that the formation of by-products is substantially suppressed. Moreover, because of the stabilizing effect of the oxygen, additional stabilization in the distillation columns can often be dispensed with. The novel process is therefore particularly simple and energy-saving.

In the Examples which follow, parts and percentages are by weight. Parts by volume bear the same relation to parts by weight as that of the liter to the kilogram.

EXAMPLE 1

The apparatus consists of 2 recycle reactors which are connected in series and have a capacity of 1000 parts by volume each, and on which distillation columns with water separators are mounted.

190 parts/hour of methacrylic acid, 5 parts/hour of sulfuric acid and 0.3 part/hour of phenothiazine are fed directly to the first recycle reactor, and 280 parts/hour of n-octanol are fed to the said recycle reactor via its distillation column. The molar ratio of methacrylic acid to octanol is 1:0.97.

In addition to the mixture discharged from the first reactor, 36 parts/hour of octanol are fed to the second reactor via its distillation column. 150,000 parts by volume/hour of air are passed through each of the reaction mixtures in the two reactors. The reaction temperature is 120° C. in each case. A total of 40 parts/hour of water are separated off via the two water separators. 470 parts/hour of mixture are discharged from the reactor, the mixture containing 90.5% of n-octyl methacrylate, 0.7% of methacrylic acid, 5.8% of octanol, 0.5% of high-boiling by-products and traces of dioctyl ether and olefins. The conversion based on methacrylic acid is 98.7 mole % and that based on octanol is 91.4 mole %, while the selectivity based on methacrylic acid is 98.2 mole % and that based on octanol is 97.3 mole %.

EXAMPLE 2

In an apparatus as described in Example 1, 172 parts/hour of methacrylic acid, 0.5 part/hour of sulfuric acid and 0.3 part/hour of phenothiazine are fed directly to the first recycle reactor, and 250 parts/hour of 2-ethylhexanol are fed to the said reactor via the distillation column. The molar ratio of acrylic acid to 2-ethylhexanol is 1:0.96. 36 parts/hour of 2-ethylhexanol are fed to the second recycle reactor via its distillation column. 150,000 parts by volume/hour of air are passed through each of the two reaction mixtures in the recycle reactors. The reaction temperature in both reactors is 120° C. A total of 35 parts/hour of water is separated off via the two water separators. 427 parts/hour of mixture are discharged from the reactor, the mixture containing 90.1% of 2-ethylhexyl methacrylate, 0.7% of methacrylic acid, 6.9% of 2-ethylhexanol, 0.8% of high-boiling by-products and traces of dioctyl ether and olefins. The conversion based on methacrylic acid is 98.2 mole % and that based on 2-ethylhexanol is 97.5 mole %, while the selectivity based on methacrylic acid is 99.2 mole % and that based on 2-ethylhexanol is 98.8 mole %.

EXAMPLE 3

An apparatus as described in Example 1 is used; 155 parts/hour of acrylic acid, 5 parts/hour of 96% strength sulfuric acid and 0.3 part/hour of phenothiazine are fed directly to the first recycle reactor, and furthermore 2,707 parts/hour of 2-ethylhexanol are introduced into the said reactor via the distillation column. In addition to the mixture discharged from the first recycle reactor, 40 parts/hour of 2-ethylhexanol are fed to the second reactor via its distillation column. Accordingly, the molar ratio of acrylic acid to 2-ethylhexanol in the first recycle reactor is 1:0.97. 150,000 parts by volume/hour of air are passed through each of the two reaction mixtures. Both recycle reactors are kept at 120° C. A total of 38 parts/hour of water is separated off via the two water separators. The mixture discharged from the second recycle reactor (430 parts/hour) contains, in addition to the stabilizer and the catalyst, 87.4% of 2-ethylhexyl acrylate, 1.1% of acrylic acid, 6.1% of 2-ethylhexanol, 0.3% of octenes, 3.3% of high-boiling by-products and traces of dioctyl ethers (less than 0.01%). The conversion based on acrylic acid is 97 mole % and that based on 2-ethylhexanol is 91.5 mole %, while the selectivity based on acrylic acid is 97.7 mole % and that based on 2-ethylhexanol is 93.5 mole %.

EXAMPLE 4

An apparatus as described in Example 1 is used; 165 parts/hour of methacrylic acid, 5 parts/hour of sulfuric acid and 0.5 part/hour of phenothiazine are fed directly to the first recycle reactor, and 350 parts/hour of n-dodecanol are fed to the said reactor via its distillation column. The molar ratio of methacrylic acid to dodecanol in the reactor is 1:0.98. In addition to the mixture discharged in the first reactor, 40 parts/hour of dodecanol are fed to the second recycle reactor via its distillation column. Moreover, 150,000 parts by volume/hour of air are passed through the reaction mixtures in the two reactors. The reaction temperature is 120° C. in each case. A total of 34 parts/hour of water is separated off via the two water separators. The mixture discharged from the reactor (0.525 part/hour) contains 89.7% of dodecanol, 0.5% of methacrylic acid, 7.7% of dodecyl alcohol, 0.9% of high-boiling by-products and traces of ether and olefins. The conversion based on methacrylic acid is 98.4 mole % and that based on dodecanol is 89.5 mole %, while the selectivity based on methacrylic acid is 98.5 mole % and that based on dodecanol is 98.2 mole %.

COMPARATIVE EXPERIMENT ACCORDING TO GERMAN PAT. NO. 2,548,561

60 parts/hour of acrylic acid, 2.2 parts/hour of sulfuric acid and 0.1 part/hour of a mixture of equal amounts of phenothiazine and hydroquinone are fed directly to a recycle reactor which has a capacity of 1000 parts by volume and on which a distillation column and water separators are mounted, and 154 parts/hour of 2-ethylhexanol are introduced into the said reactor via its distillation column. The molar ratio of acrylic acid to 2-ethylhexanol is 1:1.42. The esterification reaction is carried out at 119° C. under reduced pressure (130 mbar), the residence time being 4 hours. 15 parts/hour of water are separated off via the water separator. The mixture discharged from the reactor (201 parts/hour) contains, in addition to the stabilizers and catalyst, 70.8% of ethylhexyl acrylate, 20.6% of 2-ethylhexanol, 0.6% of acrylic acid, 0.1% of dioctyl ether, 0.6% of octenes and 6.3% of high-boiling by-products. The conversion based on acrylic acid is 98 mole % and that based on 2-ethylhexanol is 71 mole %, while the selectivity based on acrylic acid is 95 mole % and that based on 2-ethylhexanol is 91.5 mole %.

EXAMPLE 5

In an apparatus as described in Example 1, 158 parts/hour of acrylic acid, 5 parts/hour of p-toluene-sulfonic acid and 0.5 part/hour of hydroquinone monomethyl ether are fed directly to the first recycle reactor, and 178 parts/hour of 1,6-hexanediol are fed to the said reactor via the distillation column. The ratio of the number of equivalents of acrylic acid to the number of equivalents of hexanediol is 1:0.91. 150,000 parts by volume/hour of air are passed through the reaction mixtures in the two recycle reactors. The temperature in the two reactors is 110° C. A total of 35 parts/hour of water are separated off via the two water separators. The reacted mixture (246 parts/hour) contains 88.9% of 1,6-hexanediol diacrylate. The conversion based on acrylic acid is 91.7% and that based on hexanediol is 100%, while the selectivity based on acrylic acid is 95.6% and that based on hexanediol is 96.5%.

We claim:

1. A process for the preparation of an alkyl ester of $\alpha,\beta$-monoolefinically unsaturated monocarboxylic acid by esterifying the carboxylic acid with an alcohol of 6 to 20 carbon atoms in the absence of diluent in the presence of from 0.1 to 5% by weight, based on the reaction mixture, of a strong acid and in the presence of a polymerization inhibitor and an oxygen-containing gas, at from 80° to 150° C., wherein the molar ratio of the $\alpha,\beta$-olefinically unsaturated monocarboxylic acid to the alcohol is from 1:0.8 to 1:1.2, and the water of reaction is separated off from the reaction mixture by passing an inert gas containing from 1 to 20% by volume of oxygen through the reaction mixture.

* * * * *